United States Patent [19]

Kalina

[11] Patent Number: 4,743,451
[45] Date of Patent: May 10, 1988

[54] ALCOHOL PRODUCTION

[75] Inventor: Vladimir Kalina, Lausanne, Switzerland

[73] Assignee: Nestec S.A., Vevey, Switzerland

[21] Appl. No.: 895,270

[22] Filed: Aug. 11, 1986

[30] Foreign Application Priority Data

Sep. 5, 1985 [CH] Switzerland ............... 3831/85

[51] Int. Cl.$^4$ ............................................. C12G 1/02
[52] U.S. Cl. ............................................. 426/15; 426/62; 426/330.4; 426/592
[58] Field of Search ............... 426/7, 8, 11, 13, 15, 426/16, 26, 29, 62, 330.3–330.5, 330, 321, 422, 592, 599, 495, 271; 435/813

[56] References Cited

U.S. PATENT DOCUMENTS 4,329,433  5/1982  Seebeck et al. ............... 426/15

OTHER PUBLICATIONS

Amerine et al. "The Technology of Wine Making", 3rd Edition Westport, CT, AVI publ. Co., Inc. 1972 pp. 99 & 316.

Primary Examiner—Raymond N. Jones
Assistant Examiner—Marianne Cintins
Attorney, Agent, or Firm—Vogt & O'Donnell

[57] ABSTRACT

Continuous fermentation of a must by yeast in a single vat to ensure a high yield and good productivity under conditions which remain stable for long periods is obtained by inhibition of the growth of the yeast by limiting the amount of assimilable phosphate and by continuous injection of a small quantity of fresh yeast.

14 Claims, No Drawings

ALCOHOL PRODUCTION

This invention relates to a process for the production of alcohol by continuous microaerobic fermentation of a must in a fermentation vat, in which fresh must is continuously injected into the vat, fermented must is continuously run off from the vat and most of the yeast present in the must run-off is recycled into the vat.

There are various known processes for the production of alcohol by fermentation of a culture medium rich in fermentable sugars which is referred to as "must" in the present specification and claims. Some of these processes are characterized by high productivity, i.e., the hourly production of a large quantity of alcohol in relation to the volume of the installation; others are more particularly characterized by a high yield, i.e., a high conversion of the fermentable sugar into alcohol; others are suitable for working on a large scale and others yet again are characterized by a low energy consumption or by a relatively simple construction of the installation.

Processes of the high-productivity type include fermentation under reduced pressure, of which the disadvantage is of a technological nature, the installations required being complicated. High-yield processes include, for example, those which use several fermenters arranged in a cascade in which different types of yeast are successively used, the installations required again being complicated for relatively modest productivity.

In general terms, continuous fermentation with recycling of most of the yeast present in the must run-off forms the basis of the majority of known processes because it should permit a high concentration of yeast to be used in the must, which is favourable to productivity. The problems to be solved in that case are, for example, the inhibition of fermentation of the alcohol content of the must is too high, the bacteriological dangers if the alcohol content of the must is too low, the consumption of stirring energy if the viscosity of the must is too high, or if the oxygen transfer levels are too low, the reduction in yield if the yeast is poorly regenerated or the production of a superfluous quantity of yeast, if too large a quantity of oxygen is used to maintain the level of activity of the yeast in the installation.

Among the known processes, particular mention may be made of the process which is carried out using at least two successive fermentation vats, wherein the fermentation conditions in the first vat are regulated to promote rapid growth of the yeast, the fermentation conditions in the second vat are regulated to promote rapid production of alcohol and the yeast present in the must run off from the second vat is recycled to the first vat. In this known process, considerable external energy is required in the first vat to ensure an adequate oxygen transfer rate while the conditions prevailing in the second vat promote the development of irreversible respiratory problems in the yeast which cannot be remedied by recycling into the first vat. The yeast cells affected by respiratory problems continue to multiply in the first vat with production of unwanted secondary metabolites, such as glycerol or succinic acid, for example. For these reasons, this known process can only be carried out using relatively low concentrations of yeast in the must while the use of flocculating yeast does not afford any particular advantage.

Another known process, which is intended to ensure a good transfer of oxygen and to create favourable and homogeneous fermentation conditions while consuming only a minimum of external energy, is carried out in a closed circuit in a single vat surmounted by an air-lift pump operating solely under the effect of the carbon dioxide released in the vat, wherein the oxygen is injected in a minimal quantity at the top of a return pipe and is completely dissolved in the must before the must is reinjected at the bottom of the vat, a high pressure and high homogeneity of the must is ensured over the entire height of the fermentation vat by the height of the return pipe and by the presence of a back-pressure valve at the top of the fermentation vat. As the yeast used is flocculating, the separation of the yeast present in the must removed takes outside the fermentation vat in a decantation vessel under pressure, and the pressure in the decantation vessel, and likewise recycling of the yeast, again is ensured by the height of the return pipe. This known process may be carried out on a large scale with high productivity and a high yield. However, enrichment of the must with yeast cells showing degeneration of the respiratory system or even irreversible respiratory deficiency is inevitable in the long term which limits the practicable duration of a fermentation process, such as this, to approximately 1 to 2 weeks, beyond which both yield and productivity are reduced, in particular, by the production of secondary metabolites, such as, for example, glycerol or succinic acid.

The object of the present invention is to provide a process for the production of alcohol by continuous fermentation which gives a particularly good yield coupled with high long-term stability. More particularly, the object of the invention is to provide a process which may be carried out over a considerably longer period than 1 to 2 weeks without any reduction in productivity or yield.

To this end, the process according to the invention is characterized in that the growth of the yeast in the vat is inhibited by limiting the concentration of assimilable phosphate in the must and in that the yeast in the vat is regenerated by continuous injection of fresh yeast into the vat.

In the present specification and claims, "fresh yeast" is understood to be a yeast which has been obtained by aerobic fermentation and which has an intact respiratory system, in other words, high respiratory activity.

It has been found that, by limiting the concentration of phosphate in the must, it is surprisingly possible to limit the growth of the yeast used for the production of alcohol without causing the production of secondary metabolites. It is thus possible to obtain a yield, in other words a conversion factor into alcohol of the fermentable sugar contained in the must, close to the theoretical maximum, which is approximately 51% by weight. By virtue of the process according to the invention, it is possible, in particular, to obtain a yield of approximately 49%, or higher, which is better than the yields obtained with the majority of the known processes mentioned above, which are generally between about 44 and 48%. In addition, it has been found that, by simultaneously regenerating the yeast in the vat by continuous injection of fresh yeast in minimal quantities, more especially by hourly injection of a weight of fresh yeast corresponding to a fraction of % of the weight of yeast contained in the vat, it is possible to keep both the yield and the productivity at the same level virtually indefinitely and, in any case, for a considerably longer period than the 1 or 2 weeks characteristic of the maximum possible duration of the majority of the known processes mentioned above.

The present combination of the two essential features of the process according to the invention, namely, inhibition of the growth of the yeasts by limitation of the assimilable phosphate in the must and regeneration of the yeast by continuous addition of fresh yeast, thus surprisingly provides both for a particularly good yield and for high long-term stability. Another advantage of the process according to the invention is that it enables these surprising results to be obtained both with flocculating yeasts and with non-flocculating yeasts. Yet another advantage of the process according to the invention is that, in a preferred embodiment, it may be carried out using only the quantity of oxygen necessary to maintain the activity of the yeast. It is thus possible to reduce the quantity of oxygen used, even in relation to that used in the last of the known processes described above, without risking the production of unwanted secondary metabolites, such as, for example, glycerol or succinic acid.

The starting material used for carrying out the process according to the invention may be a must preferably having a fermentable sugar content of from 100 to 200 g/l in addition to the nutritive substances essential to the yeast. If the fermentable sugar content of the must is below 100 g/l, the low alcohol content of the must run-off makes the subsequent step of separation of the alcohol from the must, for example, by distillation, unnecessarily expensive. If the fermentable sugar content of the must is above 200 g/l, the high alcohol content of the must in the vat decelarates fermentation unduly and reduces productivity. A volume of fresh must corresponding to 0.1-0.3 times the volume of the must present in the fermentation vat is preferably injected hourly into the vat. If less fresh must than the smallest quantity thus defined is injected hourly, it may well be possible to work with a higher concentration of alcohol in the vat, but at too slow a tempo which reduces productivity. If more fresh must than the largest quantity thus defined is injected hourly, it is not possible to work with a sufficient concentration of alcohol in the vat which adds unnecessarily to the cost of the subsequent step of separation of the alcohol from the must.

So far as the yeast used is concerned, it may be selected from the yeasts known for their particular aptitudes for the production of alcohol. Depending on the type of fermenter used, it is possible to select a yeast known for its particular aptitude for the formation of aggregates which facilitate its sedimentation, in other words, a flocculating yeast, or a yeast which has no particular tendency to form aggregates, in other words, a non-flocculating yeast. When a flocculating yeast is used, it may advantageously be separated from the must by decantation, in particular, by decantation under pressure which compresses the carbon dioxide present in the must and prevents it from making the aggregates float. When a non-flocculating yeast is used, it may be separated from the must by centrifuging or filtration, for example.

The must in the vat may contain 30-80 g dry weight of yeast per liter. If less than 30 g/l is used, productivity is unnecessarily reduced. If more than 80 g/l is used, problems of viscosity are likely to be encountered in the vat and during separation of the yeast from the must run off.

To regenerate the yeast in the vat, i.e, to maintain the activity of the yeast in the process according to the invention, a weight of fresh yeast corresponding to approximately 0.2-0.5% of the weight of the yeast contained in the fermentation vat is preferably injected hourly into the vat. These figures correspond to a complete renewal of the yeast in the vat in the space of about 8 to 20 days.

To inhibit the growth of the yeast in the vat, the concentration of assimilable phosphate in the must is thus limited. The concentration of assimilable phosphate is preferably limited to a value of from 0.01 to 0.2 g/l in the fresh must injected. With less than 0.01 g/l, there is a risk that the desired activity of the yeast might not be maintained. With more than 0.2 g/l, there is a risk that the desired growth-inhibiting effect might not be obtained.

In a preferred embodiment of the process according to the invention, the concentration of assimilable phosphate is limited by addition to the fresh must injected or by direct injection into the vat of a soluble aluminium salt, such as aluminium sulfate or aluminium chloride, for example, in a molar concentration at least three times higher than that of the phosphate present in the fresh must. Most of the phosphate is then precipitated in the form of aluminium salt and the concentration of phosphate in solution in the must is unable to exceed a very low value which depends upon the equilibrium constant of the system. Even if the small quantities of dissolved phosphate reform as they are consumed by the yeast, the yeast has continually to make a considerable effort to find a way to that small quantity, and the growth-inhibiting effect is thus ensured.

The process according to the invention may be carried out using virtually any of the known fermentation installations designed for continuous operation. It may be carried out particularly effectively in an installation comprising a vat under pressure surmounted by an airlift pump in which the must circulates continuously in a closed circuit under the sole effect of the carbon dioxide released by the fermentation process.

The invention is illustrated by the following Examples and Comparison Example.

EXAMPLE 1

The fermenter used comprises a 15 liter fermentation vat 50 cm tall and 20 cm in diameter, means for injecting fresh must, fresh yeast and gas into the vat, means for running off fermented must and means for the removal of gas from the vat, a decantation vessel outside the vat and a yeast recycling system which is capable of keeping the weight of the yeast in the vat at a constant level.

The volume of must in the fermentation vat is kept at 10 liters. 1.35 l/h of fresh must having the following composition in g/l is injected into the vat:

| sucrose | 165 | $CaCl_2.2H_2O$ | 0.05 |
|---|---|---|---|
| yeast extract | 1 | $MnSO_4.7H_2O$ | 0.01 |
| $K_2SO_4$ | 0.5 | $FeSO_4.7H_2O$ | 0.01 |
| $MgSO_4.7H_2O$ | 0.5 | $ZnSO_4.7H_2O$ | 0.005 |
| $(NH_4)_2SO_4$ | 0.5 | $H_3PO_4$ | 0.05 |

150 ml/h of a must containing 3 g dry weight of fresh yeast are also injected into the vat. This fresh yeast is obtained by cultivating the yeast *Saccharomyces cerevisiae* CBS 2961 under aerobic conditions with a yield of 50% based on sucrose. In other words, 6 g sucrose are used to produce these 3 g dry weight of fresh yeast.

Finally, 2.4 l/h air mixed with nitrogen are injected into the vat to obtain a total of 180 liters of gas removed hourly from the fermenter. The must in the vat is stirred by means of two turbines with four 90 mm square blades rotating at 300 r.p.m. The pH of the must in the vat is kept at a constant value of 4.7 by addition of sulfuric acid or ammonia. The temperature of the must in the vat is kept at 33° C.

4 l/h of fermented must containing 65 g/l dry weight of yeast are run off from the vat. The must run-off passes to a 5 liter decantation vessel in which a pressure of 3 bar prevails. 2.5 l/h of concentrated yeast suspension are recycled into the vat while the weight of yeast contained in the vat is kept constant. 1.5 l/h of must containing per liter 70 g alcohol, less than 1 g sucrose and less than 0.5 yeast dry matter are collected.

The quantity of recoverable alcohol entrained with the gases issuing from the fermenter amounting to 6.3 g/h, a yield of 49% and a productivity of 11 g alcohol per hour and per liter effective vat volume are thus obtained. The ratio between the dry weight of fresh yeast injected and the weight of alcohol produced is below 0.03.

After 1 month's continuous operation of the fermenter under the same conditions, no reduction is observed either in yield or in productivity.

EXAMPLE 2

The procedure is as described in Example 1, except that the fresh must injected contains 0.2 g/l $H_3PO_4$ instead of 0.05 g/l, and 2.7 g/h $Al_2(SO_4)_3 \cdot 18H_2O$ are additionally injected straight into the vat, corresponding to a molar concentration of Al 3 times higher than that of $H_3PO_4$.

The yield and productivity obtained are the same as in Example 1.

COMPARISON EXAMPLE

The procedure is the same as described in Example 1, except that 2.25 l/h of fresh must containing per liter 130 g sucrose instead of 165 g and 0.8 g $H_3PO_4$ instead of 0.05 g are injected into the vat, no fresh yeast is injected and air is injected in a quantity of 90 ml/h instead of 40 ml/h.

4.75 l/h fermented must containing 50 g/l dry weight of yeast are run off from the vat. The must run-off is decanted and 2.5 l/h concentrated yeast suspension are again recycled, but on this occasion 13.8 g/h dry weight of yeast are removed from the decantation vessel. 2.25 l/h must containing per liter 55 g alcohol and also less than 1 g sucrose and less than 0.5 g yeast dry matter are collected.

The quantity of recoverable alcohol entrained with the gases issuing from the fermenter amounting to 5 g/h, a yield of 44% and a productivity of 13 g alcohol per hour and per liter effective volume of the vat are thus obtained. The ratio between the dry weight of the yeast removed and the weight of alcohol produced is 0.11.

If it is desired to obtain a higher alcohol content in the fermented must, the fermentable sugar content of the fresh must injected and the yeast content of the must in the vat have to be increased. This soon leads to problems of instability because the aeration of the must also has to be considerably increased to avoid a respiratory deficiency of the yeast which would result in a reduction in yield and productivity.

I claim:

1. A process for the microaerobic production of alcohol by continuously fermenting must in a fermentation vat, wherein fresh must is continuously injected into the vat, fermented must and yeast are continuously run off from the vat and yeast present in the must and yeast run-off is recycled into the vat, comprising limiting assimilable phosphate in the fermenting must to a concentration which maintains the yeast active but inhibits growth of yeast in the vat, and continuously injecting fresh yeast into the vat to regenerate and maintain the activity of the yeast in the vat.

2. A process as claimed in claim 1, wherein the fresh must injected into the vat has a fermentable sugar content of 100 g/l to 200 g/l and a volume of fresh must corresponding to 0.1 to 0.3 times the volume of the fermenting must present in the fermentation vat is injected hourly into the vat.

3. A process as claimed in claim 1, wherein a weight of fresh yeast corresponding to 0.2% to 0.5% of the weight of the yeast in the vat is injected hourly into the vat such that the fermenting must in the vat contains 30 g to 80 g dry weight of yeast per liter.

4. A process as claimed in claim 1, wherein the concentration of assimilable phosphate is limited to a value of from 0.01 g/l to 0.2 g/l in the fresh must injected into the vat.

5. A process as claimed in claim 1, wherein the concentration of assimilable phosphate is limited by injecting a soluble aluminum salt into the fresh must in a molar concentration at least three times higher than that of the assimilable phosphate present in the fresh must.

6. A process for the microaerobic production of alcohol by continuous fermentation of must and yeast in an apparatus including a fermenting apparatus and an apparatus to recover yeast from fermented must and recycle the yeast back to the fermenting apparatus comprising limiting the concentration of assimilable phosphate of the must to be fermented to a value of from 0.1 g/l to 0.2 g/l and injecting fresh yeast into the fermenting apparatus to regenerate and maintain the activity of the yeast in the fermenting apparatus.

7. A process as claimed in claim 6, wherein the must to be fermented has a sugar content of from 100 g/l to 200 g/l and wherein a volume of the must is injected into the fermenting apparatus hourly which corresponds to from 0.1 to 0.3 times the volume of must contained in the fermenting apparatus and wherein an amount of fresh yeast is injected into the fermenting apparatus hourly which corresponds to from 0.2% to 0.5% of the weight of the yeast contained in the fermenting apparatus to maintain 30 g to 80 g dry weight of yeast per liter of must in the fermenting apparatus.

8. A process as claimed in claim 6, wherein the concentration of phosphate is limited by adding soluble aluminum salt to the must to be fermented.

9. A process as claimed in claim 7, wherein the concentration of assimilable phosphate is limited by adding soluble aluminum salt to the must to be fermented.

10. A process as claimed in claim 8, wherein the aluminum salt injected into the fresh must has a molar concentration at least three times higher than the molar concentration of the phosphate present in the fresh must.

11. A process as claimed in claim 9, wherein the aluminum salt injected into the fresh must has a molar concentration at least three times higher than the molar concentration of the phosphate present in the fresh must.

12. A process for the microaerobic production of alcohol by continuous fermentation of must and yeast in an apparatus including a fermenting apparatus and an apparatus to recover yeast from fermented must and recycle the yeast to the fermenting apparatus comprising limiting the concentration of assimilable phosphate of must to be fermented to a value of from 0.01 g/l to 0.2 g/l, by adding a soluble aluminum salt to the must, and injecting fresh yeast into the fermenting apparatus to regenerate and maintain the activity of the yeast in the fermenting apparatus.

13. A process as claimed in claim 12 wherein the aluminum salt injected into the fresh must has a molar concentration at least three times higher than the molar concentration of the phosphate present in the fresh must.

14. A process as claimed in claim 12 wherein the must to be fermented has a sugar content of from 100 g/l to 200 g/l and wherein a volume of the must is injected into the fermenting system hourly which corresponds to from 0.1 to 0.3 times the volume of fermenting must and wherein an amount of fresh yeast is injected into the fermenting apparatus hourly which corresponds to from 0.2% to 0.5% of the weight of the yeast contained in the fermenting apparatus to maintain 30 g to 80 g dry weight of yeast per liter of must in the fermenting apparatus.

* * * * *

UNITED STATES PATENT AND TRADEMARK OFFICE
CERTIFICATE OF CORRECTION

PATENT NO. : 4,743,451

DATED : May 10, 1988

INVENTOR(S) : Vladimir Kalina

It is certified that error appears in the above-identified patent and that said Letters Patent is hereby corrected as shown below:

On the Title Page, under the heading "OTHER PUBLICATIONS", "publ." should be --Publ.--.

Column 1, line 36, "of" should be --if--.

Column 3, line 65, "i.e," should be --i.e.,--.

Column 5, line 13, after "0.5" insert --g--.

Column 6, line 35, "0.1" should be --0.01--.

Signed and Sealed this

First Day of November, 1988

Attest:

DONALD J. QUIGG

*Attesting Officer*  *Commissioner of Patents and Trademarks*